United States Patent
Shaw et al.

(10) Patent No.: US 6,537,991 B1
(45) Date of Patent: Mar. 25, 2003

(54) METHOD OF TREATING A PERIPHERAL NEUROPATHIC PAIN

(75) Inventors: John S Shaw, MacClesfield Cheshire (GB); William Bastain, Wilmington, DE (US)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/913,488

(22) PCT Filed: Feb. 11, 2000

(86) PCT No.: PCT/GB00/00439

§ 371 (c)(1),
(2), (4) Date: Nov. 15, 2001

(87) PCT Pub. No.: WO00/48446

PCT Pub. Date: Aug. 24, 2000

(30) Foreign Application Priority Data

Feb. 17, 1999 (GB) ................................................ 9903476

(51) Int. Cl.[7] .................... A61K 31/537; A61K 31/495; A61K 31/44; A61K 31/185; A61K 31/50
(52) U.S. Cl. .................. 514/236.05; 514/340; 514/354; 514/355; 514/356; 514/576; 514/247; 514/248; 514/252
(58) Field of Search ............................. 514/236.5, 252, 514/340, 354, 355, 356, 576, 247, 238

(56) References Cited

U.S. PATENT DOCUMENTS 6,242,493 B1 * 6/2001 Gareau et al. ............... 514/569

FOREIGN PATENT DOCUMENTS

| WO | WO 96/03380 | 2/1996 |
|----|-------------|--------|
| WO | WO 97/00863 | 1/1997 |
| WO | WO 97/00864 | 1/1997 |

OTHER PUBLICATIONS

Database Biosis Online! Bioscienceg Information Service, Philadelphia, PA, US; 1986 Itoh H et al : "therapeutic Effect of Prostaglandin E–1 on Diabetic Neuropathy" Database accession No. PREV198682057138, XP002152441 abstract & Journal of the Japan Diabetes Society, vol. 29, No. SUPPL. 1, 1986, pp. 88–90, ISSN: 0021–437X.

* cited by examiner

Primary Examiner—Zohreh Fay
Assistant Examiner—Brian-Yong S. Kwon
(74) Attorney, Agent, or Firm—White & Case LLP

(57) ABSTRACT

The invention provides methods for treating and preventing neuropathic pain which comprise the administration of an effective amount of an antagonist of the pain-enhancing effects of E-type prostaglandins, for example, $EP_1$-typo prostaglandin receptor antagonists, to warm-blooded animals including humans in need of such treatment. The invention also provides pharmaceutical compositions for such prevention and treatment of neuropathic pain.

3 Claims, No Drawings

METHOD OF TREATING A PERIPHERAL NEUROPATHIC PAIN

This application is the National Phase of International Application PCT/GB00/00439 filed Feb. 11, 2000 which designated the U.S. and that International Application.

This invention relates to therapeutic agents, and in particular to the use of compounds that are antagonists of the pain enhancing effects of E-type prostaglandins for the treatment or prevention of neuropathic pain. The invention also concerns the use of a compound that is an antagonist of the pain enhancing effects of E-type prostaglandins in the production of a medicament for use in the treatment or prevention of neuropathic pain. The invention further concerns a method of treating or preventing neuropathic pain by administration of an effective amount of an antagonist of the pain enhancing effects of E-type prostaglandins to a warm blooded animal such as man.

Neuropathic pain is a common clinical symptom associated with a variety of peripheral neuropathies and central nervous system injuries. Peripheral nerve injuries can arise directly from trauma, or indirectly from a wide range of diseases such as infections, cancer, metabolic conditions, toxins and musculoskeletal changes. Central nervous system injuries associated with neuropathic pain include stroke, trauma, Parkinson's disease, multiple sclerosis and syringomyelia. The symptoms and signs of neuropathic pain include spontaneous/continuous pain, heightened cutaneous sensitivity (hyperesthesia), increased sensitivity with a lowering of the threshold to noxious stimulation (hyperalgesia), continued sensation of pain after the stimulus has ceased (hyperpathia), nociceptive response to innocuous stimulation (allodynia) and the presence of sensory deficits (hypoalgesia).

The treatment of neuropathic pain represents a significant therapeutic challenge Current clinical practice includes the use of a number of drug classes for the management of neuropathic pain, for example anticonvulsants, tricyclic antidepressants, and systemic local anaesthetics. However, the usual outcome of such treatment is partial or unsatisfactory pain relief, and in some cases the adverse effects of these drugs outweigh their clinical usefulness.

Classic analgesics are widely believed to be poorly effective or ineffective in the treatment of neuropathic pain. Few clinical studies on the use of non steroidal anti-inflammatory drugs (NSAIDs) or opiates in the treatment of neuropathic pain have been conducted, but in those which have, the results appear to indicate that NSAIDs are poorly effective or ineffective and opiates only work at high doses. A review analysing the controlled clinical data for peripheral neuropathic pain (PNP) (Pain, November, 1997 73(2), 123–39) reported that NSAIDs were probably ineffective as analgesics for PNP and that there was no long-term data supporting the analgesic effectiveness of any drug.

The development of a rodent model of peripheral mononeuropathy (Pain, 33, 1988, 87–107; Exp Brain Res, 113, 1997, 200–206; and Exp Brain Res, 120, 1998, 432–438) has provided a new approach for studies of post-injury neuropathic pain. The model produces neuropathic pain syndromes in the rat by loosely ligating the common sciatic nerve and has been described as a chronic constrictive injury (CCI) model. The behavioural, morphological and autoradiographic data obtained from the rodents in this model closely represent the clinical features of post-injury neuropathic pain. For example, the anticonvulsant gabapentin demonstrates activity in the CCI model (Eur J Pharmacol, 324, 1997, 157–160) and has been evaluated against neuropathic pain in humans (JAMA. 280, 1998, 1837–42; Clin J Pain. 13, 1997, 251–5). The NSAID ketorolac tromethamine possessed modest activity compared to morphine when dosed intrathecally (Can J Anaesth, 1996, 43, 967). This model has value therefore in predicting efficacy of compounds against neuropathic pain.

This invention is based on the surprising discovery that compounds known to be antagonists of the pain enhancing effects of E-type prostaglandins have activity in the CCI model.

According to the invention, there is provided a method of treating or preventing neuropathic pain in a warm blooded animal such as a human being requiring such treatment which comprises administering to said animal a therapeutically effective amount of an antagonist of the pain enhancing effects of E-type prostaglandins, or a pharmaceutically acceptable salt or an in vivo hydrolysable ester thereof.

Typical antagonists of the neuropaihic pain enhancing effects of E-type prostaglandins useful in this invention include the following $E_1$-type prostaglandin receptor antagonists.

a) 6-[N-(2-benzyloxy-5-bromobenzyl)-N-ethylamino]pyridazine-3-carboxylic acid (disclosed as Example 15 in International Patent Application WO 96/03380);

b) 6-[N-(5-bromo-2-(2-methylprop-2-en-1-yloxy)benzyl)-N-ethylamino]pyridazine-3-carboxylic acid (disclosed as Example 15 in International Patent Application WO 97/00864);

c) N-propanesulphonyl-6-[N-(5-bromo-2-(cyclopropylmethoxy)benzyl)-N-ethylamino]pyridazine-3-carboxamide (disclosed as Example 14 in International Patent Application WO 97/00863);

d) N-(3,5-dimethylisoxazol-4-ylsulphonyl)-6-[N-(5-chloro-2-(2-methylpropoxy)benzyl)-N-ethylamino]pyridazine-3-carboxamide (disclosed as compound number 1 in Example 8 in International Patent Application WO 97/00863); and e) 6-[N-(5-bromo-2-(cyclopropylmethoxy)benzyl)-N-ethylamino]pyridazine-3-carboxylic acid (disclosed as Example 3 in International Patent Application WO 97/00863);

or a pharmaceutically acceptable salt or an in vivo hydrolysable ester thereof.

According to a further feature of the invention, there is provided a method of treating or preventing neuropathic pain in a warm blooded animal such as a human being requiring such treatment which comprises administering to said animal a therapeutically effective amount of a compound listed under paragraphs a)–e) above, or a pharmaceutically acceptable salt or an in vivo hydrolysable ester thereof.

According to a further feature of the invention, there is provided a method of treating or preventing neuropathic pain in a warm blooded animal such as a human being requiring such treatment which comprises administering to said animal a therapeutically effective amount of the compound listed under paragraph c) above, or a pharmaceutically acceptable salt or an in vivo hydrolysable ester thereof.

Further antagonists of the pain enhancing effects of E-type prostaglandins include those described in EP 0480641; EP 0534667; WO 96/03380; WO 96/06822; EPA 0733033; EPA 0847391; EPA 0835246 and EPA 0752421. The contents of the aforesaid European and International Patent Applications are hereby incorporated by reference thereto.

In addition antagonists of the pain enhancing effects of E-type prostaglandins include those described in U.S. Pat.

No. 5,504,077; EP 694546; U.S. Pat. No. 5,441,950; U.S. Pat. No. 5,420,270; U.S. Pat. No. 5,354,747; U.S. Pat. No. 5,354,746; U.S. Pat. No. 5,324,722; U.S. Pat. No. 5,304,644; U.S. Pat. No. 5,281,590; WO 9313082; EP 539977; WO 9307132; EP 512400; EP 512399; EP 218077; EP 193822; U.S. Pat. No. 4,132,847; EP 0878465; EP 0300676; U.S. Pat. No. 4,775,680; EP 0845451; EP 0160408; U.S. Pat. No. 4,820,689 and WO 9827053. The contents of the aforesaid US, European and International Patents and Applications are hereby incorporated by reference thereto.

According to a further aspect of the invention there is provided the use of a compound that is an antagonist of the pain enhancing effects of E-type prostaglandins, or a pharmaceutically acceptable salt or an in vivo hydrolysable ester thereof, for the manufacture of a medicament for use in the treatment or prevention of neuropathic pain.

According to a further aspect of the invention there is provided the use of a compound that is an antagonist of the pain enhancing effects of E-type prostaglandins for the treatment or prevention of neuropathic pain.

According to a further aspect of the invention there is provided the use of a compound that is an antagonist of the pain enhancing effects of E-type prostaglandins or a pharmaceutically acceptable salt or an in vivo hydrolysable ester thereof, for the treatment or prevention of neuropathic pain.

According to a further aspect of the invention there is provided the use of a compound listed under paragraphs a)–e) above, or a pharmaceutically acceptable salt or an in vivo hydrolysable ester thereof, for the manufacture of a medicament for use in the treatment or prevention of neuropathic pain.

According to a further aspect of the invention there is provided the use of a compound listed under paragraphs a)–e) above or a pharmaceutically acceptable salt or an in vivo hydrolysable ester thereof, for the treatment or prevention of neuropithic pain.

According to a further aspect of the invention there is provided the use of the compound listed under paragraph c) above or a pharmaceutically acceptable salt or an in vivo hydrolysable ester thereof, for the manufacture of a medicament for use in the treatment or prevention of neuropathic pain.

Preferred compounds of the invention are those listed under paragraphs a)–e) above, or a pharmaceutically acceptable salt or an in vivo hydrolysable ester thereof.

A particularly preferred compound is the compound listed under paragraph above, or a pharmaceutically acceptable salt or an in vivo hydrolysable ester thereof.

Preferred aspects of the invention relate to the uses and methods described above of the compound or a pharmaceutically acceptable salt thereof.

In cases where compounds of the invention are sufficiently basic or acidic to form stable acid or basic salts, administration of the compound as a salt may be appropriate, and pharmaceutically acceptable salts may be made by conventional methods such as those described below. Examples of suitable pharmaceutically acceptable salts are organic acid addition salts formed with acids which form a physiologically acceptable anion, for example, tosylate, methanesulphonate, acetate, tartrate, citrate, succinate, benzoate, ascorbate, maleate, α-ketoglutarate, and α-glycerophosphate. Suitable inorganic salts may also be formed such as sulphate, nitrate, hydrochloride and hydrobromide.

Pharmaceutically acceptable salts may be obtained using standard procedures well known in the art, for example by reacting a sufficiently basic compound (or its ester) with a suitable acid affording a physiologically acceptable anion. It may also be possible to make a corresponding alkali metal (e.g. sodium, potassium, or lithium) or alkaline earth metal (e.g. calcium) salt by treating a compound of the invention (and in some cases the ester) with one equivalent of an alkali metal or alkaline earth metal hydroxide or alkoxide (e.g. the ethoxide or methoxide) in aqueous medium followed by conventional purification techniques.

An in vivo hydrolysable ester of a compound of the invention containing a carboxy group is, for example, a pharmaceutically acceptable ester which is hydrolysed in the human or animal body to produce the parent acid, for example, a pharmaceutically acceptable ester formed with a $C_{1-6}$alcohol such as methanol, ethanol, ethylene glycol, propanol or butanol, or with a phenol or benzyl alcohol such as phenol or benzyl alcohol or a substituted phenol or benzyl alcohol wherein the substituent is, for example, a halo (such as fluoro or chloro), $C_{1-4}$alkyl (such as methyl) or $C_{1-4}$alkoxy (such as ethoxy) group. The term also includes α-acyloxyalkyl esters and related compounds which break down to give the parent hydroxy group. Examples of α-acyloxyalkyl esters include acetoxymethoxycarbonyl and 2,2-dimethylpropionyloxymethoxycarbonyl.

In use, an antagonist of the pain enhancing effects of E-type prostaglandins, or a pharmaceutically acceptable salt or an in vivo hydrolysable ester thereof, will generally be administered for its treatment or prevention of neuropathic pain in a warm-blooded animal such as man requiring such treatment, in the form of a conventional pharmaceutical composition, for example, as may be described in the relevant published European, US or International patent applications referred to above, and generally the composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square metre body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–500 mg of active ingredient.

Therefore according to a further feature of the invention there is provided a pharmaceutical composition which comprises an antagonist of the pain enhancing effects of E-type prostaglandins or a pharmaceutically acceptable salt or an in vivo hydrolysable ester thereof, in association with a pharmaceutically acceptable excipient or carrier for the treatment or prevention of neuropathic pain.

The identification of compounds which are useful in the treatment or prevention of neuropathic pain is the subject of the present invention. These properties may be assessed, for example, using the CCI model as described in Pain, 33, 1988, 87–107.

In that model, the compound described in paragraph d) above demonstrates activity at oral test doses of 0.3, 3 and 30 mg/kg/day (dosed four times a day).

Antagonists of the pain enhancing effects of E-type prostaglandins may be used in the treatment or prevention of neuropathic pain in single therapeutic agent therapy or in combination therapy. Combination therapy may involve current conventional therapeutic agents used in the management of neuropathic pain such as anticonvulsants, tricyclic antidepressants and systemic local anaesthetics. Combination therapy may also involve the use of a locally applied local anaesthetic.

Combination therapy may also involve conventional NSAIDs such as indomethacin, ketorolac, acetylsalicylic acid, ibuprofen, sulindac, tolmetin and piroxicam or COX-2 inhibitors such as celecoxib or rofecoxib. Combination therapy may also involve an opiate.

For the avoidance of doubt, where the treatment or prevention of neuropathic pain is referred to, this includes the associated symptoms and signs of neuropathic pain. The neuropathic pain may also be of central or peripheral origin.

What is claimed is:

1. A method of treating a peripheral neuropathic pain in a warm-blooded animal requiring such treatment which comprises administering to said animal a therapeutically effective amount of an $EP_1$-type prostaglandin receptor antagonist selected from the group consisting of:

6-[N-(2-benzyloxy-5-bromobenzyl)-N-ethylamino]pyridazine-3-carboxylic acid;

6-[N-(5-bromo-2-(2-methylprop-2-en-1-yloxy)benzyl)-N-ethylamino]pyridazine-3-carboxylic acid;

N-propanesulphonyl-6-[N-(5-bromo-2-(cyclopropylmethoxy)benzyl-N-ethylamino]pyridazin-3-carboxamide;

N-(3,5-dimethylisoxazol-4-ylsulphonyl)-6-[N-(5-chloro-2-(2-methylpropoxy)benzyl)-N-ethylamino]pyridazin-3-carboxamide;

6-[N-(5-bromo-2-(cyclopropylmothoxy)benzyl)-N-ethylamino]pyridazine-3-carboxylic acid; and pharmaceutically acceptable salts and in vivo hydrolysable esters thereof.

2. The method according to claim 1 wherein the $EP_1$-type prostaglandin receptor antagonist is N-propanesulphonyl-6-[N-(5-bromo-2-(cyclopropylmethoxy)benzyl-N-ethylamino]pyridazine-3-carboxamide, or a pharmaceutically acceptable salt or in-vivo hydrolysable ester thereof.

3. A method according to claim 1, wherein the peripheral neuropathic pain is a post-injury peripheral neuropathic pain.

* * * * *

UNITED STATES PATENT AND TRADEMARK OFFICE
CERTIFICATE OF CORRECTION

PATENT NO.    : 6,537,991 B1
DATED         : March 25, 2003
INVENTOR(S)   : Shaw et al.

It is certified that error appears in the above-identified patent and that said Letters Patent is hereby corrected as shown below:

Title page,
Item [56], References Cited, OTHER PUBLICATIONS, "Bioscienceg" should read -- Biosciences --; and "therapeutic" should read -- Therapeutic --.

Column 2,
Line 21, delete "." and substitute therefor -- ; --.

Column 6,
Lines 4 and 9, (2 instances), delete "pyridazin" and substitute therefor -- pyridazine --.

Signed and Sealed this

Twelfth Day of August, 2003

JAMES E. ROGAN
*Director of the United States Patent and Trademark Office*